(12) United States Patent
Sieburg

(10) Patent No.: US 7,103,398 B2
(45) Date of Patent: Sep. 5, 2006

(54) ELECTRICAL SENSING AND/OR SIGNAL APPLICATION DEVICE

(75) Inventor: Willi Sieburg, Oststeinbek (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/399,358

(22) PCT Filed: Nov. 1, 2000

(86) PCT No.: PCT/EP00/10775

§ 371 (c)(1),
(2), (4) Date: Apr. 14, 2003

(87) PCT Pub. No.: WO02/36002

PCT Pub. Date: May 10, 2002

(65) Prior Publication Data

US 2004/0210122 A1    Oct. 21, 2004

(51) Int. Cl.
*A61B 5/04* (2006.01)
*A61N 1/04* (2006.01)
(52) U.S. Cl. .................. 600/393; 607/115; 607/148; 29/825
(58) Field of Classification Search .......... 600/393; 607/115, 148
See application file for complete search history.

(56) References Cited

U.S. PATENT DOCUMENTS 3,490,439 A    1/1970   Rolston (Continued)

FOREIGN PATENT DOCUMENTS

DE    U 8502291    6/1985

(Continued)

OTHER PUBLICATIONS

M. Klein, et al., "*Single Chip Bumping*", Technical University of Berlin, Center of Microperipheric Technologies, Berlin, Germany, and Fraunhofer Institute for Reliability and Microintegration IZM Berlin, Germany. Paper consists 6 pgs. (Publication date not known, but is before the priority date of the present application.).

(Continued)

*Primary Examiner*—Lee S. Cohen
(74) *Attorney, Agent, or Firm*—Melanie G. Gover

(57) ABSTRACT

The electrical signal sensing and/or signal application device for sensing electrical signals on a surface and/or for applying electrical signals to a surface, particularly of human or animal skin or other organs or tissues, comprises a substrate (12) having first and second major surfaces (14), and a plurality of electrodes (16) arranged on the first major surface (14) of the substrate (12) and projecting therefrom, each of the electrodes (16) comprising a pointed contact end (36) facing away from the substrate (12) for contacting the surface, and a base end (26) facing towards the substrate (12). On the first or second or both major surfaces (14) of the substrate (12) there is arranged a plurality of first contact pads (22) for electrical connection to contact elements of an evaluation and/or driving means for evaluating the sensed electric signals and/or applying signals to the electrodes (16), the first contact pads (22) being electrically connected to the electrodes (16). The first major surface (14) of the substrate (12) comprises, for each electrode (16), a second contact pad (18) the base ends (26) of the electrodes electrically and mechanically connected to the second contact pads (18). Each electrode (18) is generated by bonding an electrically conductive bonding wire to a second contact pad (18) for generating a thickened socket portion (24) of the electrode comprising its base end (26), and by tearing the bonded bonding wire off the socket portion (24) so as to generate a pointed portion (34) of the electrode (16) comprising its pointed contact end (36) and projecting from the socket portion (24) thereof.

11 Claims, 6 Drawing Sheets

U.S. PATENT DOCUMENTS

| | | |
|---|---|---|
| 3,896,790 A | 7/1975 | Dikmen |
| 4,353,372 A | 10/1982 | Ayer |
| 4,926,879 A * | 5/1990 | Sevrain et al. ............... 607/152 |
| 4,969,468 A * | 11/1990 | Byers et al. ................. 600/393 |
| 5,143,079 A | 9/1992 | Frei et al. |
| 5,184,620 A | 2/1993 | Cudahy et al. |
| 5,215,088 A | 6/1993 | Normann et al. |
| 5,361,760 A * | 11/1994 | Normann et al. ........... 600/377 |
| 5,452,718 A | 9/1995 | Clare et al. |
| 5,482,038 A | 1/1996 | Ruff |
| 5,509,822 A | 4/1996 | Negus et al. |
| 5,810,742 A | 9/1998 | Pearlman |
| 5,928,159 A | 7/1999 | Eggers et al. |
| 5,928,458 A | 7/1999 | Aschenbrenner et al. |
| 6,055,448 A | 4/2000 | Anderson et al. |
| 6,128,521 A | 10/2000 | Marro et al. |
| 6,745,062 B1 * | 6/2004 | Finneran et al. ............ 600/393 |

FOREIGN PATENT DOCUMENTS

| | | |
|---|---|---|
| DE | U 9218879 | 3/1996 |
| EP | 0 538 739 B1 | 12/1994 |
| EP | 0 533 487 B1 | 3/1996 |
| WO | WO 87/07825 | 12/1987 |
| WO | WO 97/47235 | 12/1997 |
| WO | WO 98/09155 | 3/1998 |

OTHER PUBLICATIONS

R. Aschenbrenner, et al., *"Flip Chip Attachment Using Non-Conductive Adhesives and Gold Ball Bumps"*, Paper presented to International Electronics Packaging Conference, Altanta, Georgia, Sep. 25-28, 1994. Paper consists 14 pages.

J. Eldring, et al., *"Flip Chip Attachment using Mechanical Bumps"*, Paper published by Semiconductor Technology Center, Inc., 1994, ITAP & Flip Chip Proceedings, pp. 74-81.

TransScan Research and Development Co., Ltd., Product Data and Brochure with review by Food and Drug Administration, Apr. 16, 1999. Found at http://www.imaginis.com/t-scan/references.asp?mode=1.

A. J. Bruce, et al., *"Overview of Skin Cancer Detection and Prevention for the Primary Care Physician"*, Mayo Clinic Proc., Mayo Foundation for Medical Education and Research, May 2000; vol. 75: pp. 491-500.

* cited by examiner

ELECTRICAL SENSING AND/OR SIGNAL APPLICATION DEVICE

FIELD OF THE INVENTION

The invention relates to an electrical signal sensing and/or signal application device for sensing electrical signals on a surface and/or for applying an electrical signal to a surface. Such a device in particular is used for sensing electrical signals on and/or for applying electrical to human or animal skin and most preferably are used in therapy and diagnostic methods. For example a signal sensing device can be used to record impedances or other electrical images of tissues and other components or objects to which the sensing device can be electrically attached. On the other side the device can be used to apply electric current or voltage for stimulating tissues or other components or objects.

Moreover, the invention relates to a method for manufacturing a device as described above. Finally, the invention also relates to the use of such a device for therapy and diagnostic methods.

BACKGROUND OF THE INVENTION

Medical diagnosis is utilizing diverse approaches of obtaining images of humans and animals such as X-ray, computer tomography, nuclear-spin-resonance and ultrasonics. The straight forward photography is of lesser importance as it merely records the external appearance of skin portions of humans and animals while the other methods present specific views especially of the inner portions of the body which are more suitable for the diagnosis.

More recently the recording of impedance and other electrical images was developed. The use of single electrodes including the independent handling of several electrodes for the recording of the electrical properties such as the impedance typically as a function of time is well known for many decades, especially in the fields of electro-cardiography (ECG or EKG) and electro-encephalography (EEG). In these cases typically the individual electrodes are attached to the skin by some means such as suction devices or adhesives. Furthermore, these electrodes are provided with a relatively large surface having the order of magnitude of about 1 sq. cm which consists of metals, conductive gels or conductive adhesives. Typically the electrical properties are recorded as a function of time. However, the recent developments utilizes arrays of these electrodes where each of them records the electrical properties such as the impedance or conductivity in a manner that all these values are simultaneously recorded and for example brought onto a display like a monitor. This then provides images yielding information which is significantly different from the images of the other diagnostic methods as stated above. The known specific configurations will be referred to in more detail below.

A particular area of interest is the diagnosis of cancer where it is of interest to investigate the skin primarily related to breast cancer and skin cancer. The article "Overview of Skin Cancer Detection and Prevention for the Primary Care Physician" by A.3. Bruce et al. of the Mayo Clin. Proc. 2000; 75; 491–500 describes the diagnostic possibilities for a primary evaluation of the skin with respect to the detection of specific cancers. This article states that the initial visual inspection by the physician is a meaningful first step in order to decide whether or not further investigations will be necessary. However, it is desirable after the immediate first visual inspection to develop another rather simple method for identifying whether or not cancer can be diagnosed.

WO-A-97/47235 provides a method of a dermal diagnostic analysis through the use of a digital camera which allows a somewhat more sophisticated approach through the recording of the critical portions of the skin.

WO-A-98/09155 shows a step further, it includes to apply a chemical to the critical skin area and after several hours this area is illuminated with ultraviolet light and the fluorescent irradiation can be recorded through picturing spectroscopy. This allows to identify cancerous portions of the skin. This method, however, is time consuming and cumbersome and still requires additional diagnostic methods in most of the cases.

A number of possibilities have become known which utilize the determination of the electrical properties of the skin.

U.S. Pat. No. 5,928,159 describes an apparatus and methods utilizing a probe provided with several electrodes which is applied to a skin portion that might be cancerous and the electrical data of these portions are recorded in comparison with a normal neighbour portion of skin.

U.S. Pat. No. 5,143,079 describes an apparatus for the detection of tumors in tissues. It utilizes a probe with a fixed arrangement of electrodes, e.g. 64 elements arranged in an 8×8 array. These electrodes have a hexagonal form, the electrodes being of gold plated printed copper for example. The hexagons typically have sides of 10 mm. These electrodes by themselves are still rather large so that only a fairly small number of them can be utilized in the probe and, therefore, a real image cannot be generated.

A further development is described in U.S. Pat. No. 5,810,742 and the article "T-SCAN™ as a Diagnostic Tool for Breast Cancer" by M. Assenheimer et al. accessible in the Internet through www.transscan.co.il/publication1.html. The described systems have a fairly large number of individual electrodes allowing to generate an image of having a reasonable resolution. The electrodes described are typically in a rectangular array with a multiplicity of wells which are separated by dividers consisting of insulating material. These wells are filled with a hydro-gel or conductive gel and the wells themselves are provided with a metal electrode which projects to the portion below the electrode so that the entire configuration can be applied onto a printed circuit board (PCB) which has a corresponding array of electrodes. In this manner a discardable article is generated. This is of importance as for well known reasons it is not advisable to use electrode configurations for more than a single patient. The PCB as such has an array of conductive paths which are guided to a multi-pin connector which then is connected through a cable to the evaluation computer which is capable of recording the electrical characteristics of each individual electrode so that the desired image can be generated in the computer and displayed on the monitor. The use of wells filled with a conductive gel has the disadvantage of being difficult to manufacture thus being expensive which is critical for such a discardable article. Furthermore, the spacing between these wells is limited which reduces the resolution of the desired image. This is of particular importance as critical skin portions which might be cancerous only have dimensions of a few millimeters and, therefore, for obtaining a good resolution pitches of the wells in the order of several tenths of a millimeter are required.

The use of multiple electrodes or arrays of electrodes is well known and described in a large number of publications.

U.S. Pat. No. 3,490,439 describes an assembly of electrodes used for electro-encephalography. The electrodes as such are small foam balls coated with a conductive cloth piece.

U.S. Pat. No. 5,452,718 presents an electrode configuration in which a conductive material having a tip is embedded in a plastic ferrule.

U.S. Pat. No. 3,896,790 relates to a brain wave sensor in which a single electrode is used which consists of several prongs which ensure a good electrical contact, even in the presence of hair.

In the above cited references all these electrodes essentially are still separate from each other. Configurations are also known in which a multiplicity of electrodes is arranged in a fixed mutual configuration. This is described for example in U.S. Pat. No. 5,184,620, U.S. Pat. No. 4,353,372 and U.S. Pat. No. 6,055,448. In all these cases the electrodes are embedded into a common carrier, however, they are still used for the typical ECG or EEG application which means that despite their fixed spacial relationship they are individually used and usually only their time dependence is recorded.

In all electrodes and electrode arrays described above configurations are shown in which the electrodes themselves have a relatively large surface and they are typically directly applied to the outer surface of the skin. There are alternative methods of utilizing electrodes which essentially consist of individual needles. These needles operate in a somewhat different manner. If properly applied they allow to penetrate the outermost portion of the skin and provide a more valuable determination of the electrical properties which for the recording of the image appears to be advantageous.

A needle electrode is described in U.S. Pat. No. 5,482,038 where an individual sharp needle is inserted into a special holding device which allows to establish a defined pressure. Needles of this type are used for example in neurological examinations using an electro-myograph (EMG).

Similar configurations can be taken from the references U.S. Pat. No. 5,509,822 and EP-A-0 533 487 which are either used for electro-myography or for electro-cardiography. These needles are either a multiplicity of several components that are handled independently but connected to a common monitoring system or configurations in which a pair of needles is used.

EP-A-0 538 739 describes an array of needles, the number ranging between 50 and 150. These needles are brought into a common plastic holder. The needles themselves have a solid configuration with a relatively sharp pin similar to those used in acupuncture. Each needle is provided with a spring allowing to apply all needles with a given pressure. The array is a pre-determined geometrical configuration typically having an overall circular circumference. The data, however, are collected individually from each electrode and utilized in some kind of a statistical evaluation. There is no intention to record an image. Furthermore, the reference is silent with respect to the establishment of the electrical contacts between these needles and the cable leading to the electronic evaluation unit.

DE-U-92 18 879 relates to an array of electrodes for the determination of the distribution of electrical potentials on the skin of a patient. It shows multiplicities of electrodes for the above described purpose and the object of this reference is to replace this multiplicity of electrodes by a foil having semi-conductive layers which is scanned for example by a laser beam causing a temporary conductivity of a small portion of the foil thus replacing a multiplicity of electrodes by such a foil which is scanned through point by point. No reference is made at all to the type of electrode configurations used.

DE-U-85 02 291 describes arrays of needle electrodes for biomedical applications where each electrode is individually connected to a cable so that a multiplicity of signals can be recorded. No reference is made to the possibility of recording an electrical image.

WO-A-87/07825 describes an electrode and the related method of manufacture. A base carrier contains an arrangement of conducting protuberances arising from the base serving as the electrodes. These electrodes are individually connected to an electrical path that is leading to an array of contact areas which allow to transfer the signal to a recording unit. The protuberances or needles have the shape of cones. These cones are grown on a multi-layer configuration and typically have dimensions up to 25 microns. This means that they are relatively small and their primary use is in the area of neurology. The needles allow to penetrate the surface of the tissue to be diagnosed.

U.S. Pat. No. 5,215,088 describes a three-dimensional multi-electrode device especially useful as a neuron interface. The electrodes are electrically isolated from each other, the signals are typically transmitted using a multiplexing circuitry. The needles typically consist of semi-conductive material on the basis of silicon. In a block of such material sequences of cuts are obtained using a saw utilized in the microelectronic industry. This is performed in two directions so that an array of pins is obtained having a rectangular or square cross-section. In a subsequent etching process material is taken away from the upper portions of these columns so that they obtain a needle-like form. This is particularly suitable for neuron-type applications e.g. a prosthesis for a blind person. The process is rather complicated and thus expensive, needle arrays of this configuration do not appear to be suitable as single use throw-away articles because of the high cost.

Arrays of needles as electrodes require to bring them into a defined array by simultaneously electrically isolating them from each other. For instance this could be performed by bringing a multiplicity of contact pins into a plastic body, for example through an injection molding or casting method. The use of these techniques, however, is cumbersome and not very cost effective which is critical for an article that preferably should be discardable. The problem becomes even more critical when moving in the direction of smaller pitches, for example well below 1 mm. The handling of individual needles or pins will be increasingly difficult thus resulting in unacceptably high manufacturing cost.

Arrays of needles or needle-like configurations are of primary interest for the medical diagnosis and therapy of the skin or other organs and tissues of humans and animals. Such an array of electrodes, however, might also be useful for other configurations whenever it is possible to establish electrical contact with the component to be investigated and when the determination of an impedance or electrical image provides meaningful information. This typically applies to components which do not have a hard outer surface because in this case only individual electrodes would establish an electrical contact. Therefore, components of interest are typically softer on their surface like elastomeric and similar components.

SUMMARY OF THE INVENTION

Accordingly, there is a need for an electrical signal sensing and/or signal application device for sensing electrical signals on a surface and/or for applying electrical signals to a surface, particular human or animal skin or other organs or tissues which device is provided with an array of electrodes which can be reliably manufactured with a very small pitch in a cost efficient manner.

In a first aspect of the invention there is provided an electrical signal sensing and/or signal application device for sensing electrical signals on a surface and/or for applying electrical signals to a surface, particularly of human or animal skin or other organs or tissues, wherein the device comprises a substrate having first and second major surfaces, a plurality of electrodes arranged on the first major surface of the substrate and projecting therefrom, each of the electrodes comprising a pointed contact end facing away from the substrate for contacting the surface, and a base end facing towards the substrate, and a plurality of first contact pads arranged on said first or second or both major surfaces of said substrate for electrical connection to contact elements of an evaluation and/or driving means for evaluating the sensed electric signals and/or applying signals to said electrodes, said first contact pads being electrically connected to said electrodes, wherein said first major surface of said substrate comprises, for each electrode, a second contact pad said base ends of said electrodes being electrically and mechanically connected to said second contact pads, and wherein each electrode is generated by bonding an electrically conductive bonding wire to a second contact pad for generating a thickened socket portion of said electrode comprising its base end, and by tearing the bonded bonding wire off the socket portion so as to generate a pointed portion of said electrode comprising its pointed contact end and projecting from the socket portion thereof.

On the first or second or both major surface of the substrate there is arranged a plurality of first contact pads for electrical connection to contact elements of an evaluation and/or driving means for evaluating the sensed electric signals and/or applying signals to the electrodes, the first contact pads being electrically connected to the electrodes.

The first major surface of the substrate comprises, for each electrode, a second contact pad the base ends of the electrodes electrically and mechanically connected to the second contact pads.

Each electrode is generated by bonding an electrically conductive bonding wire to a second contact pad for generating a thickened socket portion of the electrode comprising its base end, and by tearing the bonded bonding wire off the socket portion so as to generate a pointed portion of the electrode comprising its pointed contact end and projecting from the socket portion thereof.

According to the invention, for the electrodes it is suggested to utilize a technology which is known from the electronic industry, namely to use so-called ball bumps. Electronic chips and especially flip chips are provided with external contact areas which by some means have to be connected to a printed circuit board (PCB) and one way to achieve this is to utilize these ball bumps. These are generated from extremely thin wires consisting of gold or gold alloys that have a diameter below 50 microns, typically 25 microns. Through the use of a special equipment the ends of these wires are pressed on one of the components to be connected, either the contact area in the chip or the corresponding contact area in the PCB. Heat is applied electrically sufficient to deform the end of the thin wire and establish a mechanical and electrical connection. Subsequently the wire is torn apart which creates a needle-like pointed configuration. After having provided all contact areas with these ball bumps the other component, either the flip chip or the PCB, is then pressed onto the arrangement of the bumps. This pressure is so high that the needle-like tips of the bumps are deformed so that also an electrical and mechanical connection is established. Needle-like configurations are not considered to be ideal and there are approaches where it is attempted to avoid them or at least flatten them.

In contrary to the use of ball bumps in the electronic industry it is now suggested to take advantage of the needle-like pointed tips of the ball bumps. In the invention these bumps are created in exactly the same manner as for the application in the electronic industry and in particular are thermally or ultrasonically or both bonded to second contact pads of a flexible or rigid substrate. By this procedure an electrode in the form of a so-called ball bump is generated on a second contact pad of the substrate wherein the ball bump electrode comprises a thickened socket portion comprising the base end for electrically and mechanically contacting the second contact pad and a needle-like pointed portion comprising the pointed contact end of the electrode projecting from the socket portion. In the invention, the ball bumps are applied to e.g. a (rigid) printed circuit board or flexible circuit (i.e. the substrate) that has a pre-determined array of conductive paths or traces whereby, however, the board or carrier could be any other configuration that includes these paths. The bumps are attached to the end areas of these conductive paths and it is ensured that the pointed configuration is created without deformation for flattening them which in this case is a desired feature. It is advantageous to increase the size of the ball bumps which, however, depends on the practical application.

The substrate with the conductive paths may be mechanically relatively unstable. For example it could consist of a flexible circuit, i.e. of a flexible layer having electrically conductive traces and pads on it and may also comprise electric or electronic components for some reason. Therefore, it is advantageous to provide the system with additional mechanical stability and, for example, the substrate of the conductive traces with the ball bumps applied onto could be supported by a plate which is appropriately attached to it providing the necessary mechanical stability. The plate can consist of plastic or metal provided that the electrical circuits are not irritated. Instead of a plate also a completely solid component preferably consisting of plastic could be used.

The substrate can be rigid (e.g. PCB), flexible (e.g. flexible circuit layer) or a ceramic material. The conductive traces or paths may extend over the surface of or through the substrate or both. In case that the electrodes and the contact pads for connecting the substrate to a processing device are on different major surfaces of the substrate, the contact pads most preferably are aligned or flush with the electrodes wherein the conductive paths directly extend through the substrate.

In another configuration a hand-held device could be used which comprises a handle that is provided at its distal end with an array of electrical contacts which for example could be a ball grid array (BGA). The handle at the other end is provided with the cable which is electrically connected to the contact array, the cable guiding the electrical information onto the evaluation unit consisting of a computer and a display.

Preferably, a discardable unit is created. This unit includes the configuration with the conductive traces like a PCB onto which the ball bumps are attached with means for providing the sufficient mechanical stability and contact means for the electrical and mechanical connection to a processing unit. This is particularly useful for the typical applications in the medical field where it is strongly advised to use such an electrode array for a single patient only. Therefore the discardable portion should only contain the absolute minimum of components to fulfil the task.

In another aspect of the invention there is provided a method for manufacturing an electrical signal sensing and/or signal application device for sensing electrical signals to a surface and/or for applying an electrical signal to a surface, particularly of human and animal skin or other organs or tissues, the method comprising the steps of
providing a substrate having first and second major surfaces,
forming first and second contact pads on the first or the second or both major surfaces of the substrate,
providing electrically conductive traces at the substrate for electrically connecting the first and second contact pads,
forming protruding electrodes onto the second contact pads by bonding a bonding wire to each of the second contact pads for generating a socket portion of the respective electrode bonded to the second contact pad, and by tearing the bonded bonding wire off the respective socket portion so as to generate pointed portions of the electrodes protruding from the socket portions thereof.

According to a third aspect of the invention the device as described above is used for biomedical applications, in particular for dermal diagnostic and for sensing and/or stimulating biologic tissue or organs or cells.

According to the invention there are provided an array of pointed electrodes and a method of producing the same which are electrically insulated with respect to each other and which simultaneously are connected to conductive traces of a substrate such as a printed circuit board or a flexible circuit, whereby the manufacture of such an electrode array including the connection means can be achieved in a cost efficient manner.

BRIEF DESCRIPTION OF THE DRAWING

The invention will be described in more detail referring to the drawing in which.

DETAILED DESCRIPTION OF PREFERRED EMBODIMENTS

Figure 1:
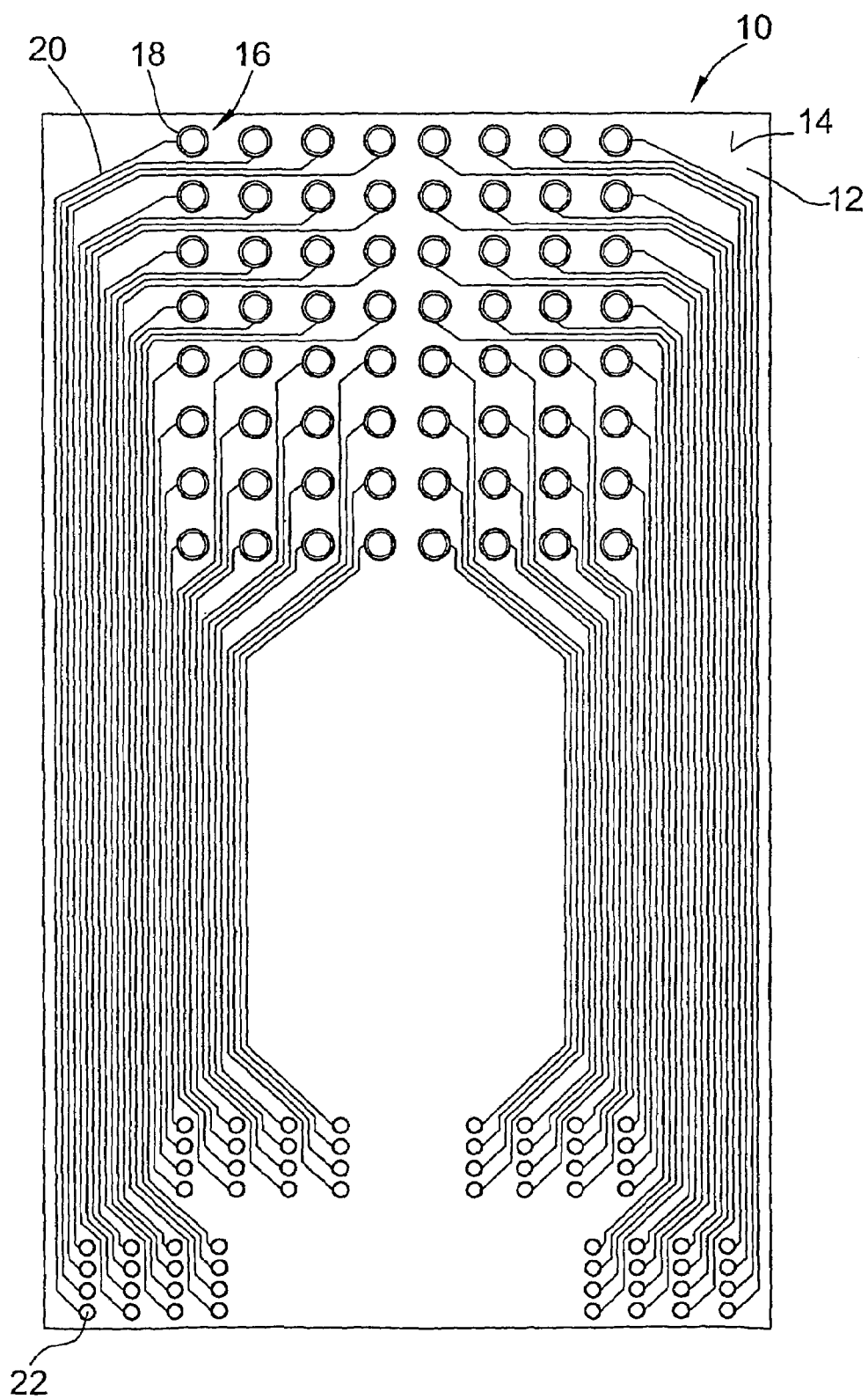
FIG. 1 is a plan view onto a substrate having an array of ball bump electrodes according to a first embodiment of the invention.

FIG. 1 shows a device 10 according to the invention and represents a view onto a circuit substrate 12 which can be a solid printed circuit board or a flexible circuitry. On one of the major surfaces 14 of the substrate 12 an array of e.g. 8×8 electrodes 16 and electrode contact pads 18 of the substrate 12 can be identified, each of them being connected with its own conductive trace 20. It is to be noted that an array of 8×8 electrodes is just a specific example and that it is advantageous and desirable to increase the number of electrodes to, for example, 16×16 corresponding to 256 individual electrodes. Even a higher number could be used. This is possible and also realistic in view of the low manufacturing cost when using the technology as suggested in the invention. The electrodes 16 as such are provided as so-called ball bumps as described hereinbelow and used in the microelectronic industry for connecting chips using the flip chip technology.

Figure 2:
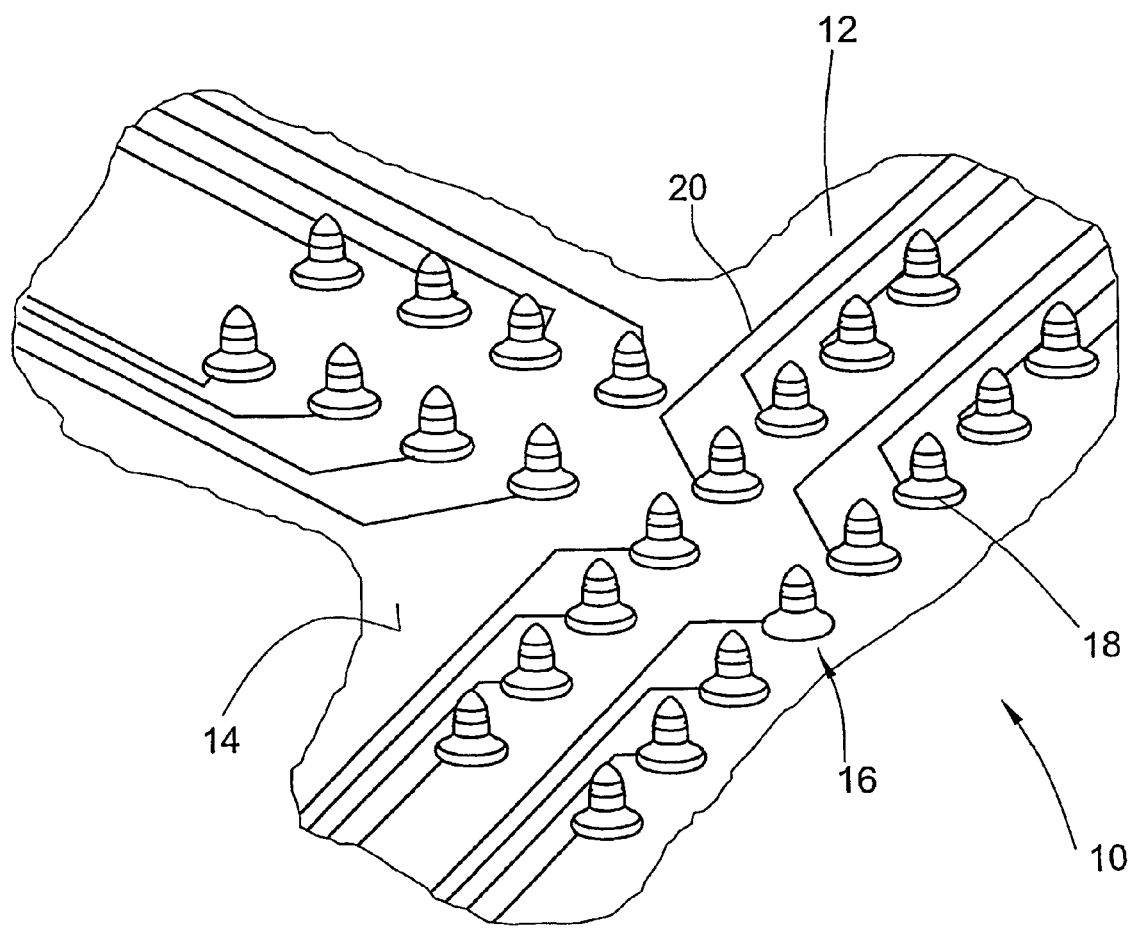
FIG. 2 is a perspective view of a portion of the ball bump electrode array according to FIG. 1.

In FIG. 2 a perspective view of a part of the electrode array on a larger scale is shown. Each conductive trace 20 leads to a first contact pad 22 (see FIG. 1) which by some connection means is connectable to an electronic device for generating and evaluating electrical signals to be applied to or sensed by the individual electrodes 16. These electrical signals can represent impedances, currents, voltages, potentials, AC or DC or impulse signals. The connection means can comprise a ball grid array (BGA), a land grid array (LGA) or contact pins and the like.

Figures 3, 4:
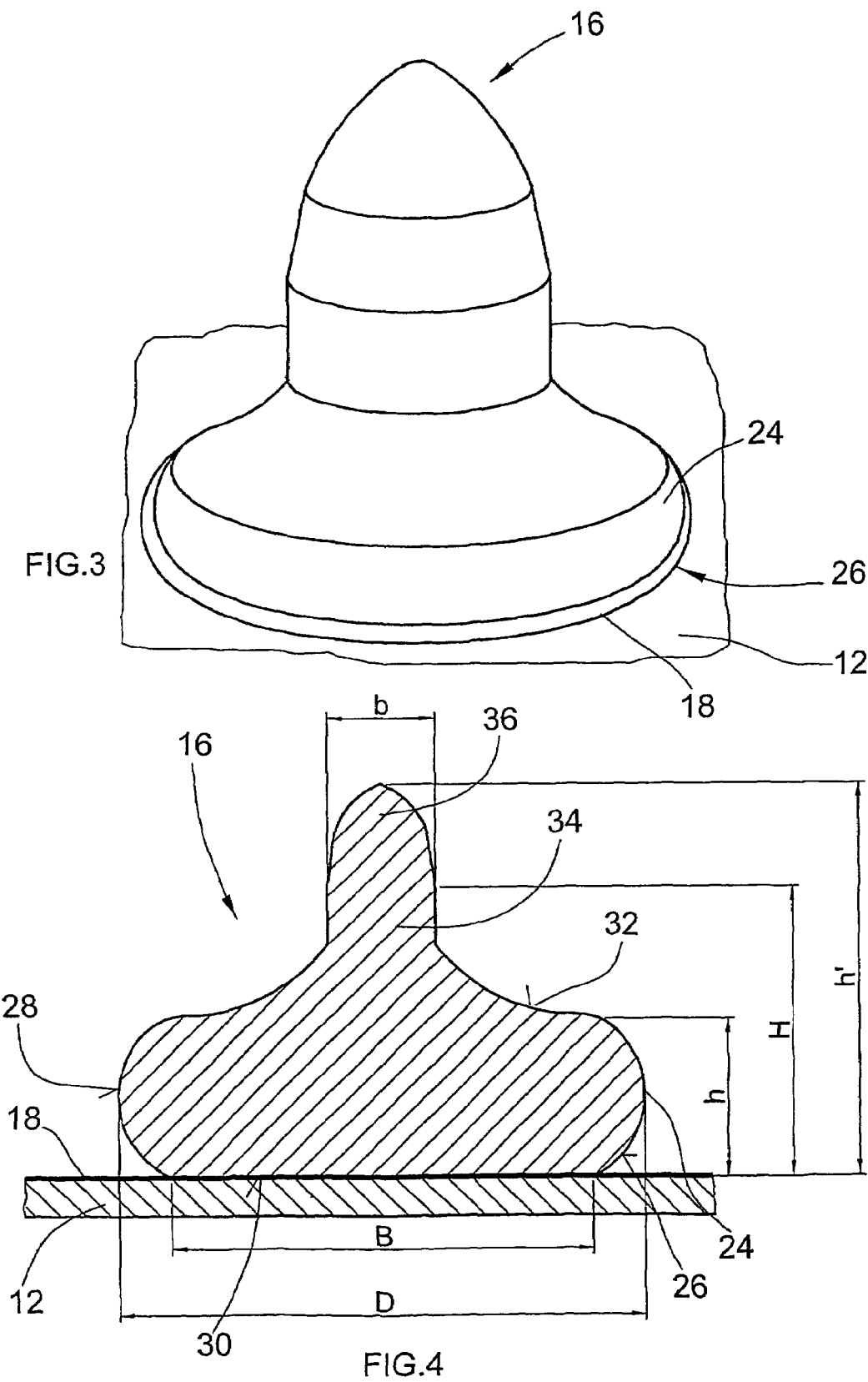
FIG. 3 is a perspective view onto a ball bump like electrode on a larger scale for illustrating the overall shape of the electrode.
FIG. 4 is a elevational view of the electrode of FIG. 3.

FIGS. 3 and 4 show in more detail the design and construction of a ball bump electrode 16. This electrode 16 comprises a thickened socket portion 24 having a base end 26 for electrically and mechanically connecting the socket portion 24 to an electrode contact pad 18. The shape of the socket portion 24 looks like a flattened ball having a rounded periphery 28, wherein the lower side 30 of the socket portion 24 being flat so as to contact the second contact pad 18. In the middle from the upper side 32 of the socket portion 24 there protrudes a pointed portion 34 having a pointed end 36. This pointed portion 34 contacts the surface (human or animal skin or organ or tissue or cell) to be measured or investigated.

It is to be noted that FIGS. 3 and 4 schematically show the ball bump which as of yet is used in the flip chip technology for connecting chips to a circuitry layer with the structured side of the chip facing the circuitry layer. In particular the pointed portion 34 can be longer and more needle-like or sharper or both than depicted. The related technology for generating such bumps and the typical use is described in a number of articles, for example "Flip Chip Attachment Using Mechanical Bumps" by J. Eldring et al., 1994, ITAP & Flip Chip Proceedings, pages 74–81, "Flip Chip Attachment Using Non-Conductive Adhesives and Gold Ball Bumps" by R. Aschenbrenner et al. from the Technische Universität Berlin, Forschungsschwerpunkt Technologien der Mikroperipherik, TIB 4/2-1, or "Single Chip Bumping" by Matthias Klein et al., Technical University of Berlin, Center of Microperipheric Technologies. The latter article describes the typical technology in more detail. Thin wires of Au98Pd for example, with diameters between 18 and 33 micrometers are grabbed by a wire clamp and pressed on the contact area to be connected. These contact areas can either be located on the flip chip or the component, comprising the conductive paths such as a PCB. This can be done utilizing a conventional ball-wedge bumping process, namely a wire bonder, for example available from F&K Delvotech Bondtechnik GmbH, Germany. The wire is passed through a capillary tube which forms the wire clamp and an electrical discharge is applied which forms a ball establishing the electrical and mechanical connection to the contact area to be connected. This is identical to the well known wire bonding technique. In a second step, however, the wire is torn off whereby it is ensured that this rupture occurs within the heat effective zone where the grain structure of the wire is coarser compared to the non-affected state. The rupture causes a lengthening of the wire with a significant simultaneous reduction of its diameter until it becomes so thin that it ruptures. In this way a pointed configuration is obtained which actually for the intended purpose of the electrical connection is undesirable.

The effect of such a process can be seen from FIG. 3 which shows a perspective view of such a mechanically applied gold stud bump on an aluminium pad. FIG. 4 shows a cross-sectional view showing the typical dimensions. The overall diameter D of the ball bump ranges between 40 and 105 microns. The actual con-tact area B (base end 26) on the contact pad 18 to be contacted is typically 80 percent of the dimension D. The height h of the socket portion 24 as shown in FIG. 4 typically ranges between 12 and 65 microns. The height H is about 10 microns larger. The overall height h' of the ball bump typically corresponds to the diameter D of the entire ball bump. In this application heights of 100–200 microns are advantageous for an optimum penetration of the pointed portion 34 and the pointed end 36 into the skin. Namely, the outermost portion of the skin typically has a thickness of around 100 microns which should be penetrated to establish a good electrical contact. The actual pointed end 36 occurs in the upper part, namely in that part of the overall height h' that exceeds H. The dimension b is around half to ⅓ of the height h of the socket portion 24. The above mentioned article refers to specific details of the ball bump in flip chip technology application. For example it has been shown that the connection to the contact pad 18 is sufficiently stable. Shear values in the area of 43–60 cN/bump have been observed. Alternative alloys are PbSn2, PbSn61, and SnAg3 and relatively pure gold itself.

Figure 5:
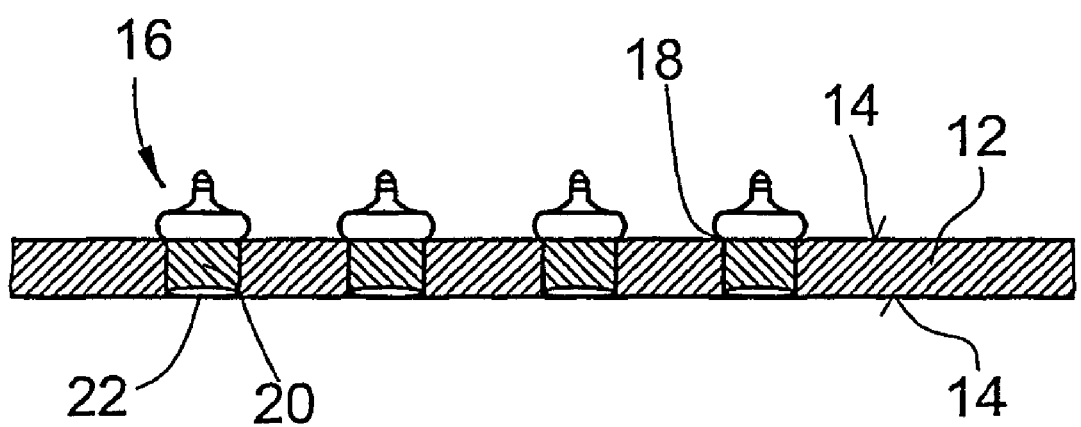
FIG. 5 shows an second embodiment of the device according to the invention.

FIG. 5 shows another embodiment of the device according to the invention. This embodiment is rather similar to that of FIGS. 1 and 2. The difference between these embodiments can be seen in the fact that in the embodiment of FIG. 5 the conductive traces 20 extend through the substrate 12 in the thickness direction thereof with the end surfaces of the conductive traces 20 laying in the first and second major surfaces 14 of the substrate 12 forming the second contact pads 18 and the first contact pads 22.

Figure 6:
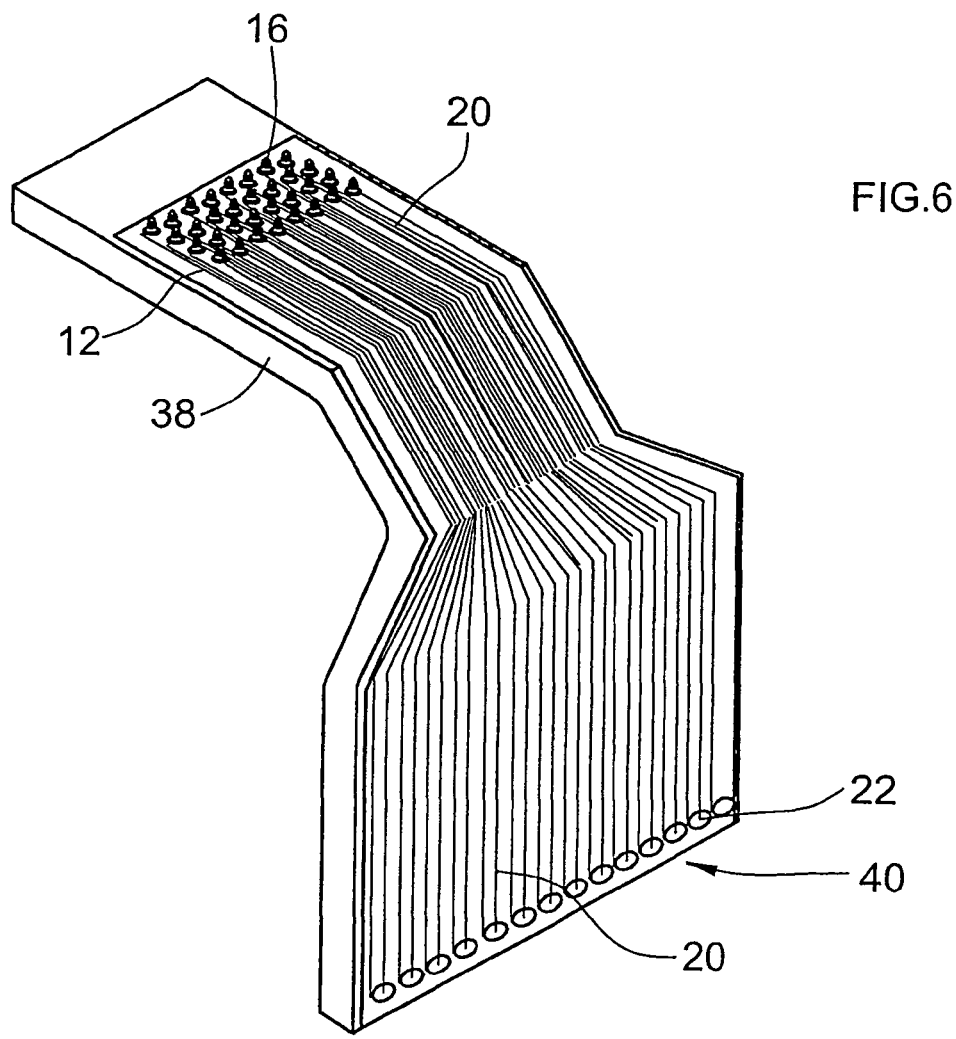
FIG. 6 shows an alternative embodiment of a device according to the invention.

FIG. 6 shows an alternative embodiment having is a configuration that in principle is similar to the one depicted in FIGS. 1 and 2, however, arranged in a non-flat configuration. Also here ball bump electrodes 16 have been applied to contact pads of the flexible substrate 12. The substrate 12 is supported by a metal 38 stiffener which is arranged so that the conductive traces 20 cannot be irritated as they are on the side 14 of the substrate 12 facing away from the metal stiffener 38. The contact area with the contact pads 22 can be a zebra strip, a ball grid array (BGA), or a land grid array (LGA) 40.

Figure 7:
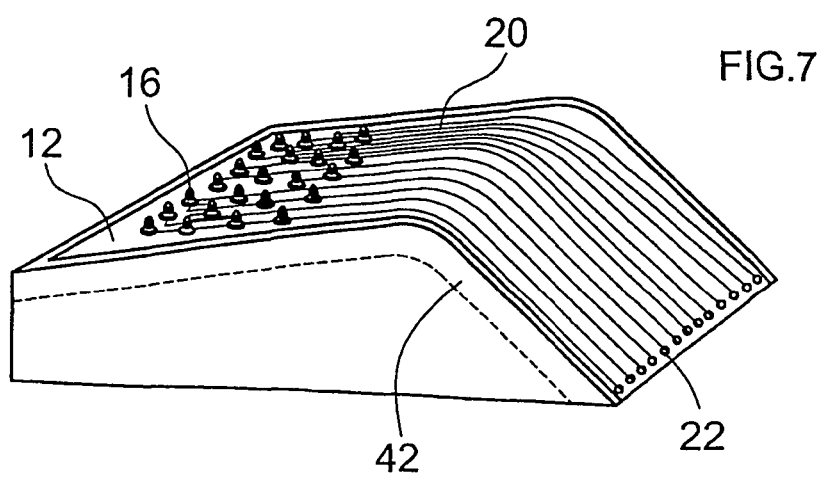
FIG. 7 shows a further embodiment of the device of the invention.

FIG. 7 shows an embodiment which is very similar to the one shown in FIG. 6 with the essential difference that instead of providing a metal plate as a stiffener a plastic body 42 is applied which is solid in itself the whole system, however, being essentially identical to the one shown in FIG. 6.

Figure 8:
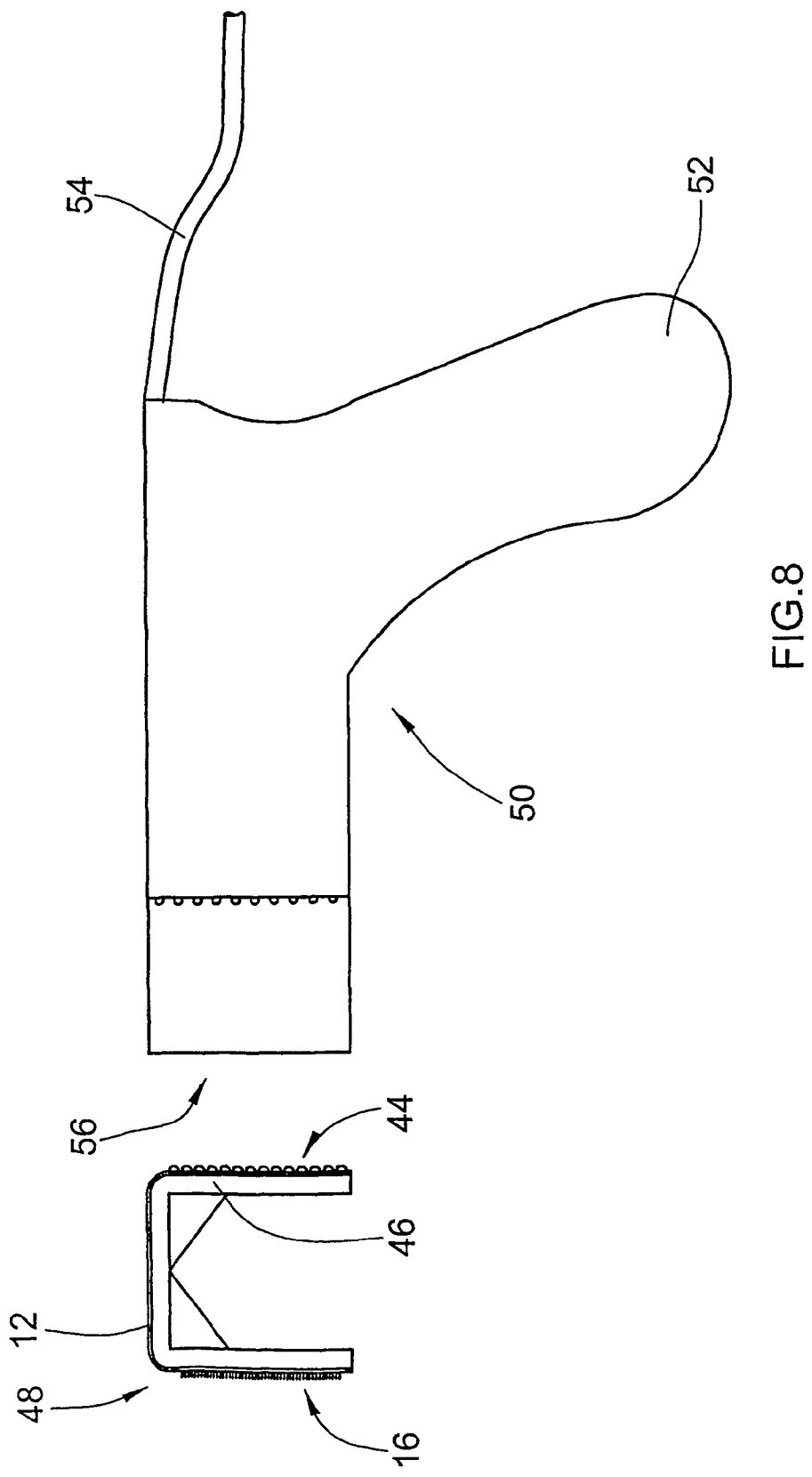
FIG. 8 shows still another alternative embodiment according to the invention.

FIG. 8 shows an alternative embodiment in which the component with the ball bump electrodes 16 is configured in a way to be discardable. The ball bump electrodes 16 are applied to a flexible circuit layer substrate 12 having BGA or LGA contact areas 44. The substrate 12 is fixed onto a plastic or metal support part 46. The discardable component 48 can be attached to a hand-held device 50. Accordingly this device 50 has to comprise mechanical features like snapping means and the like (not shown) which allow to fix the discardable component 48 onto the hand-held device 50 keeping it in a position stable enough for the intended evaluation such as the generation of an electrical or impedance image of a skin portion of a patient. The hand-held device 50 includes the handle 52 as such which can be of a pistol type. Furthermore, it includes a cable 54 connected to the connecting means 56 of the hand-held device 50 for connection to the BGA or LGA contact areas 44 of the discardable component 48. At its other end (not shown) the cable 54 is connected or connectable to an evaluation unit, typically a computer and a display unit.

The invention claimed is:

1. An electrical signal sensing and/or signal application device for sensing electrical signals on a surface and/or for applying electrical signals to a surface, of human or animal skin or other biological organs or tissues, comprising
   a substrate having first and second major surfaces,
   a plurality of electrodes arranged on the first major surface of said substrate and projecting therefrom, each of said electrodes comprising a pointed contact end facing away from said substrate for contacting the surface, and a base end facing towards said substrate, and
   a plurality of first contact pads arranged on said first or second or both major surfaces of said substrate for electrical connection to contact elements of an evaluation and/or driving means for evaluating the sensed electric signals and/or applying signals to said electrodes, said first contact pads being electrically connected to said electrodes,
   wherein said first major surface of said substrate comprises, for each electrode, a second contact pad, said base ends of said electrodes being electrically and mechanically connected to said second contact pads, and
   wherein each electrode is generated by bonding an electrically conductive bonding wire to a second contact pad for generating a thickened socket portion of said electrode comprising its base end, and by tearing the bonded bonding wire off the socket portion so as to generate a pointed portion of said electrode comprising its pointed contact end and projecting from the socket portion thereof.

2. The electrical signal sensing and/or signal application device according to claim 1, wherein said substrate is flexible.

3. The electrical signal sensing and/or signal application device according to claim 1, wherein said substrate is rigid.

4. The electrical signal sensing and/or signal application device according to claim 1, wherein said second contact pads are electrically connected to the first contact pads of said substrate via electrically conductive traces arranged on said substrate.

5. The electrical signal sensing and/or signal application device according to claim 1, wherein said first contact pads are arranged on said second major surface of said substrate and flush with the second contact pads and are electrically connected to said second contact pads by conductor portions extending though said substrate.

6. The electrical signal sensing and/or signal application device according to claim 1, wherein said socket portions of said electrodes are connected to said second contact pads by thermal bonding or ultrasonic bonding or both.

7. The device according to claim 1 in a biomedical apparatus.

8. The device according to claim 7 wherein the biomedical apparatus is a dermal diagnostic device.

9. The device according to claim 7 wherein the biomedical apparatus does one or both of sensing and stimulating matter selected from the group consisting of biological tissue, organs, and cells.

10. A method for manufacturing an electrical signal sensing and/or signal application device for sensing electrical signals to a surface and/or for applying an electrical signal to a surface, of human or animal skin or other biological organs or tissues, said method comprising the steps of providing a substrate having first and second major surfaces, forming first and second contact pads on said first or said second or both major surfaces of said substrate, providing electrically conductive traces at said substrate for electrically connecting said first and second contact pads, forming protruding electrodes onto said second contact pads by bonding a bonding wire to each of said second contact pads for generating a socket portion of the respective electrode bonded to said second contact pad, and by tearing said bonded bonding wire off said respective socket portion so as to generate pointed portions of said electrodes protruding from said socket portions thereof.

11. The method according to claim 10, wherein said bonding wire is thermally bonded or ultrasonically bonded or both to said second contact pads of said substrate.

* * * * *